United States Patent [19]

Gupta

[11] Patent Number: 4,813,956
[45] Date of Patent: Mar. 21, 1989

[54] METHOD OF FORMING SINGLE-PIECE INTRAOCULAR LENS AND CORE MEMBER AND LENS FORMED THEREBY

[75] Inventor: Amitava Gupta, Pasadena, Calif.

[73] Assignee: Ioptex Research, Inc., Azusa, Calif.

[21] Appl. No.: 34,349

[22] Filed: Apr. 3, 1987

[51] Int. Cl.⁴ .......................... A61F 2/16; B29D 11/00
[52] U.S. Cl. ........................................ 623/6; 623/901; 264/1.7
[58] Field of Search ............................ 623/6, 4, 5, 901; 351/162, 163; 264/1.1, 1.7

[56] References Cited

U.S. PATENT DOCUMENTS

| | | | |
|---|---|---|---|
| 3,034,403 | 5/1962 | Neefe | 623/4 X |
| 4,102,567 | 7/1978 | Cuffe et al. | 351/162 X |
| 4,676,791 | 6/1987 | LeMaster et al. | 623/6 |
| 4,687,485 | 8/1987 | Lim et al. | 623/6 |

Primary Examiner—Ronald L. Frinks
Attorney, Agent, or Firm—Robert R. Meads

[57] ABSTRACT

A method of forming single-piece intraocular lenses comprising the steps of forming a thin sheet of colored polymethyl methacrylate, coring the sheet to form holes therein, filling the holes with a clear or differently colored PMMA material, polymerizing the colored and clear or differently colored PMMA material comprising the sheet and filled holes, cutting core members from the polymerized sheet each having an inner circular region of PMMA material and an outer region of colored PMMA material and machining a single-piece intraocular lens from a core member to have a central lens body of PMMA material and colored PMMA positioning loops extending from and integral with the central lens body.

8 Claims, 4 Drawing Sheets

METHOD OF FORMING SINGLE-PIECE INTRAOCULAR LENS AND CORE MEMBER AND LENS FORMED THEREBY

BACKGROUND OF INVENTION

The present invention relates to a method of forming a single-piece polymethyl methacrylate (PMMA) intraocular lens (IOL) having a central lens body and colored positioning loops extending therefrom and to a PMMA core member and lens formed in and by the method.

One-piece IOLs are widely used for implantation in both anterior and posterior chambers of the eye. Such single-piece IOLs are commonly fabricated of PMMA, a polymer which is known for its long term stability and biocompatibility. Currently, all such IOLs are constructed of a clear or colorless transparent PMMA, which may be formulated with a UV-absorber to protect the retina of the eye from ultraviolet radiation present in solar flux.

Clear transparent IOLs, particularly those implanted in the capsular bag or sulcus of the eye are difficult to visualize and manipulate during implantation. For this reason, it is common in the case of IOLs having separate positioning loops staked or otherwise secured to the central lens body of the IOL, for the positioning loops to be formed of a colored material. Examples of such IOLs are the Styles 30, 31 and 34S manufactured by McGahn Medical/3M, the Model G704M Capsulform lens manufactured by IOLAB, and the Model PC-80 lens manufactured by American Medical Optics. The colored positioning loops of such lenses are readily visible and easy to manipulate during implantation. To date, however, commercially available single-piece IOLs, particularly those fabricated of PMMA, have not included colored positioning loops. Hence, such IOLs are difficult to visualize and manipulate during implantation.

SUMMARY OF INVENTION

The present invention provides a method for simply and reliably forming single-piece PMMA IOLs having colored positioning loops which are readily visible and easy to manipulate during implantation of the IOL thereby insuring accurate placement and centration of the lens.

Generally speaking, the method of the present invention comprises the following steps:

(1) Forming a thin sheet of colored PMMA;
(2) Coring the sheet to form holes therein;
(3) Filling the holes with a clear or differently colored PMMA material;
(4) Polymerizing the colored and clear or differently colored PMMA materials comprising the sheet and filled holes;
(5) Cutting core members from the polymerized sheet, each having an inner circular region of clear or differently colored PMMA material and an outer region of colored PMMA material integral with the inner region; and
(6) Machining a core member to form a single-piece IOL having a central lens body of clear or differently colored PMMA and positioning loops of colored PMMA material extending from the central lens body.

The core members and IOLs formed in and by the method are important elements of the present invention.

DETAILED DESCRIPTION OF INVENTION

Figure 1:
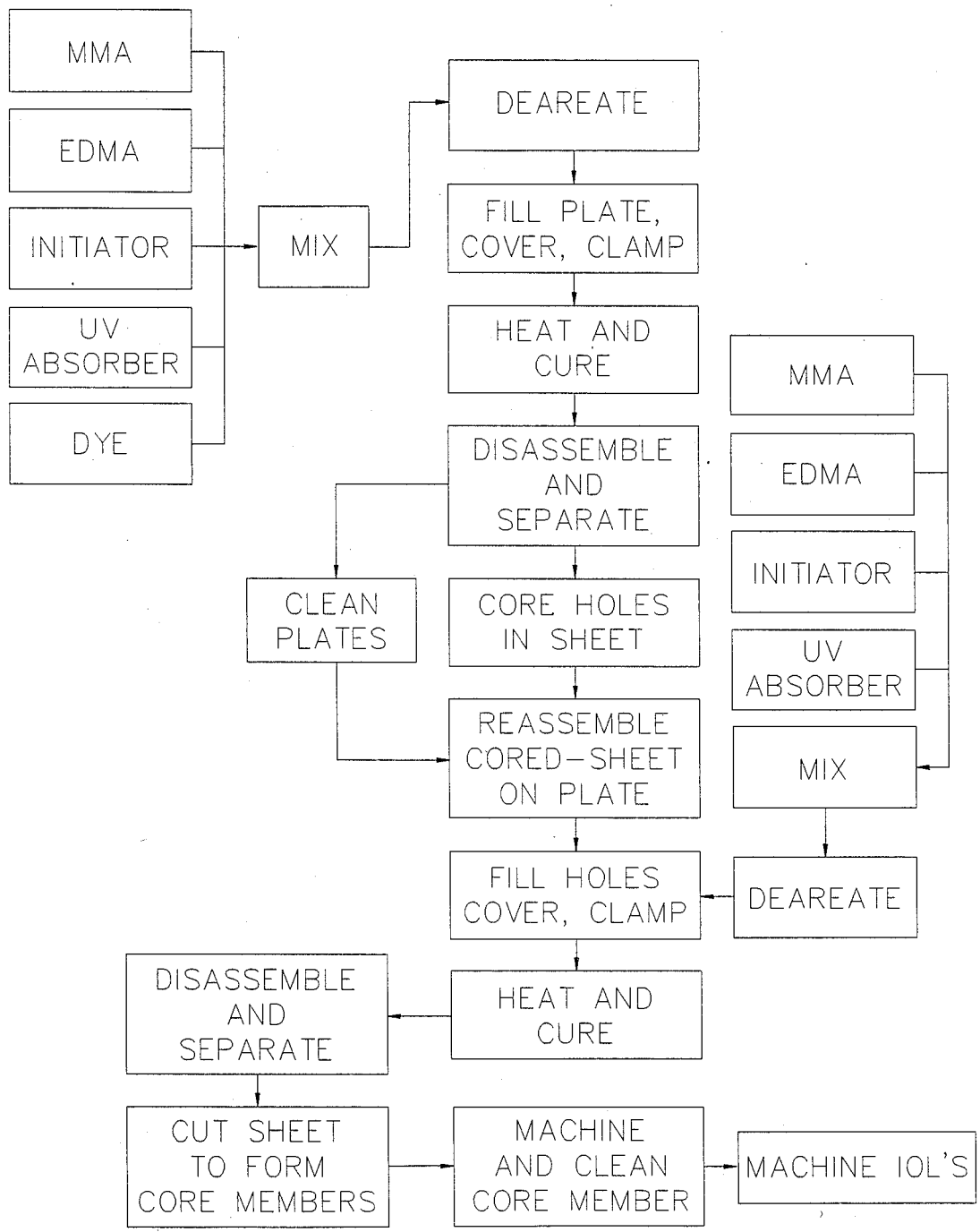
FIG. 1 is a flow diagram of one embodiment of the method of the present invention.

A preferred embodiment of the method of the present invention is illustrated in flow-diagram form in FIG. 1.

Generally speaking, as illustrated in FIG. 1, the method of the present invention comprises the steps of forming a thin sheet of colored PMMA, coring the sheet to form holes therein, filling the holes with a clear or differently colored PMMA material, polymerizing the colored and clear or differently colored PMMA material comprising the sheet and filled holes, cutting core members from the polymerized sheet each having an inner circular region of clear or differently colored PMMA and an outer region of colored PMMA integral with the inner region, and machining the core members to form single-piece IOLs each having a central lens body of clear or differently colored PMMA material and positioning loops of colored PMMA material extending from and integral with the central lens body. FIGS. 2A, 2B, 3A, 3B, and FIG. 4 depict typical core members and an IOL formed during and by the method described hereinabove.

More particularly, in a preferred embodiment of the method of the present invention, methyl methacrylate (MMA), ethylene glycol dimethacrylate (EDMA), a free radical polymerization initiator, a polymerizable UV-absorber, and a dye material are mixed. By way of example, the free radical polymerization initiator may comprise USP-245. Examples of other usable initiators are (1) other peroxides such as Lupersol 101$^{tm}$ (DuPont), (2) Azoisobutyronitrile (AIBN), and (3) Cumene Hydroperoxide. By way of example, the polymerizable UV-absorber may be 2-hydroxy, 4-ethyloxyacryloxy benzophenone (UV-2098). Other examples of useful UV-absorbers are 2(2'-hydroxy 5'-vinylphenyl) 2H-benzotriazole, Permasorb MA (tm) (Hexcel Corporation). By way of example, the dye material may comprise a blue dye such as tetra n-butyl phthalocyanato copper (II). Examples of other useful dye materials are D and C Green No. 6 (tm) (Pylam Chemical Company).

With the foregoing materials and following the methods set forth in FIG. 1, an example of the formation procedure may comprise the mixing of 100 g of distilled methyl methacrylate with 5 g of distilled ethylene glycol dimethacrylate, 0.5 g of USSP-245, 1.5 g of UV-2098 and 1 mg of the blue dye material. After mixing, the mixture may be deareated and poured as a sheet into the shallow well of a glass plate such as a 6"×6" tempered glass plate which has been thoroughly cleaned and edged on all four sides with a semisoft gasket material approximately 1" thick. After the well has been filled with the mixture to form a sheet, the sheet may be closed at the top by a second clean tempered glass plate and the two plates clamped together. The resulting package may then be placed in an oven for heating, curing, and polymerization of the monomer mixture. For example, the package may be heated at 60° C. for 12 hours and then for an additional 4 hours at 90° C. Following heating and curing, the package is removed from the oven, the clamps loosened and the glass plates separated to expose a clear blue PMMA sheet. The sheet may be removed from the package and holes formed therein as by standard coring methods to produce a regular array of holes which may be approximately 8 mm in diameter. The cored sheet then may be placed on a clean glass plate having a gasket around its marginal edge and the holes filled with a monomer mixture formed as described above without the blue dye or with a different dye. For example, as illustrated in FIG. 1, the mixture may consist of methyl methacrylate, ethylene glycol dimethacrylate, free radical polymerization initiator and the polymerizable UV-absorber. After mixing, the monomer mixture may be deareated and poured into the holes formed in the sheet supported on the clean glass plate. A clean glass plate may be placed over the cored sheet and the stack clamped together as before. The resulting package then may be placed in an oven and cured in the same manner as previously described to effect a polymerization of the clear or differently colored and colored PMMA to form a one piece integral sheet. After heating and curing, the plates may be separated as before and the polymerized sheet of PMMA material withdrawn therefrom and cut into core members which may be in the form illustrated in FIGS. 2A and 2B, and 3B.

Figure 2A:
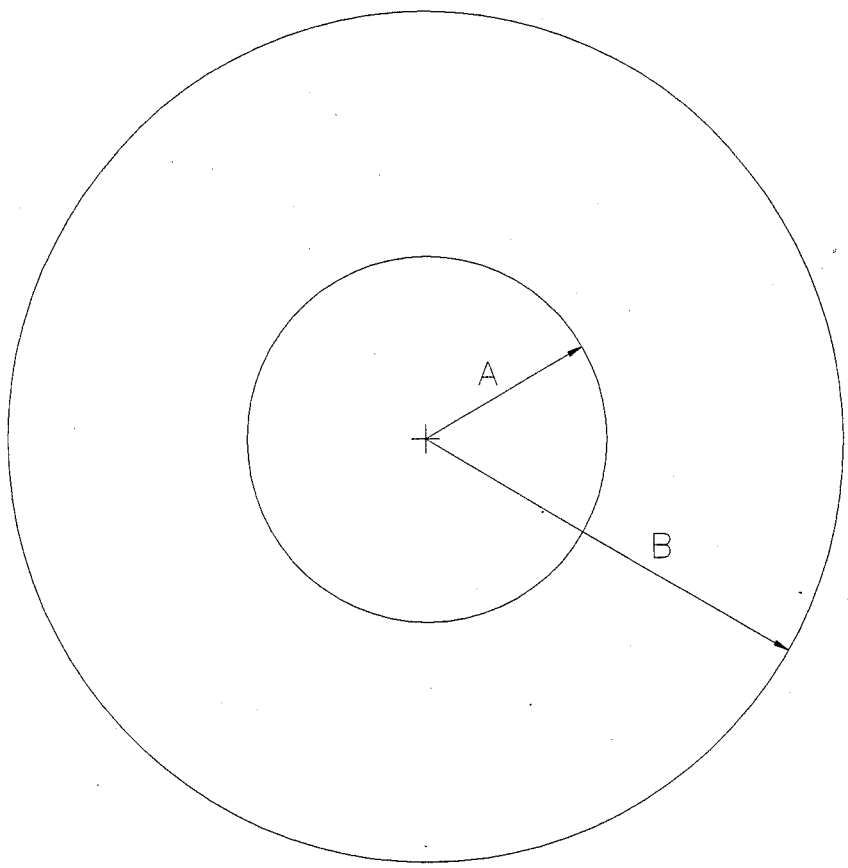
FIGS. 2A and 2B are plane and side views, respectively, of a core member formed in the method of the present invention.
Figure 2B:
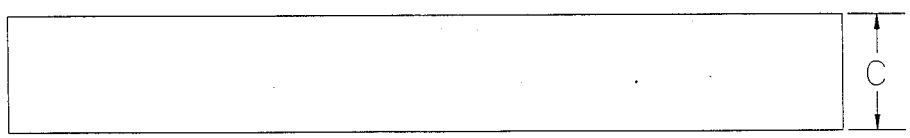

As represented in FIGS. 2A and 2B, the core member may have a thickness of between 2 mm and 6 mm (dimension C) and may include an inner flat circular region of clear polymethyl methacrylate having a radius A of between 4 mm and 8 mm surrounded by an outer flat region integral therewith formed of a colored PMMA material and having an outer radius of between 8 mm and 20 mm.

Figure 3A:
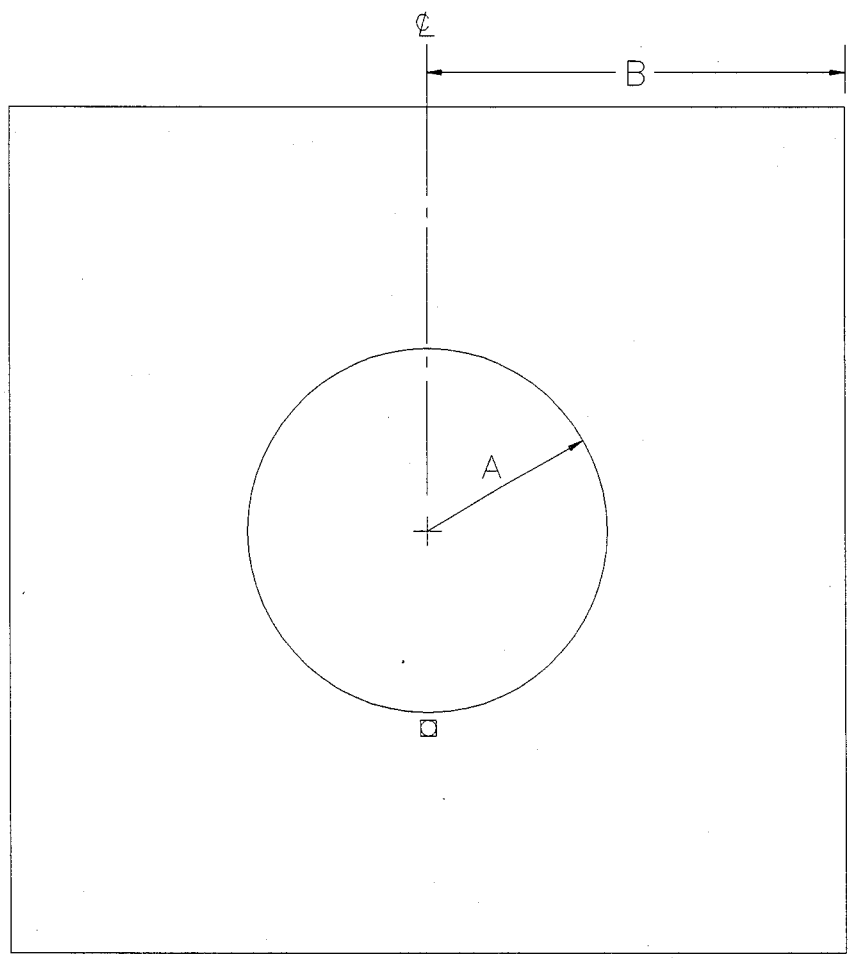
FIGS. 3A and 3B are plane and side views, respectively, of another core member formed in the method of the present invention.
Figure 3B:

Alternately, as illustrated in FIGS. 3A and 3B, the resulting core members cut from the polymerized sheet of PMMA material may have a rectangular form between 16 mm and 40 mm square with a thickness C of between 2 mm and 6 mm, an inner flat circular region having a radius of between 4 mm and 8 mm and a dimension B between center and edge of between 8 mm and 20 mm. As with the core member of Figures 2A and 2B, the core member of FIGS. 3A and 3B has an inner circular region of clear polymethyl methacrylate and an outer flat region integral with and surrounding the inner region and formed of a colored PMMA material.

Figure 4A:
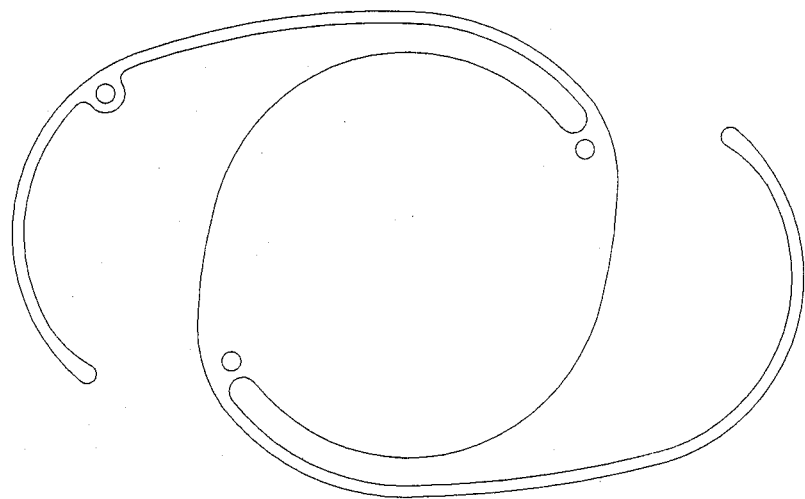
FIGS. 4A and 4B are plane and side views, respectively, of a single-piece PMMA IOL formed by the method of the present invention including a central lens body of PMMA material and colored PMMA positioning loops integral with and extending from the central body.
Figure 4B:

Returning to the method of FIG. 1, the core members may be cleaned and machined of all irregularities and then further machined by conventional and well known methods to form an IOL of single-piece construction, such as illustrated in FIGS. 4A and 4B. As illustrated, such an IOL comprises a central lens body of PMMA material and positioning loops extending from the central lens body and formed of colored PMMA material. Since the positioning loops are colored, they are readily visible and easily manipulated during implantation of the IOL to provide for accurate placement and centration of the lens during implantation.

While a specific lens composition has been described hereinabove, a more general composition for the core members may be as follows:
inner circular region:
methyl methacrylate equal or greater than 90% by weight;
ethylene glycol dimethacrylate equal to or less than 5% by weight;
UV-absorber equal to or less than 5% by weight;
outer region:
methyl methacrylate equal to or greater than 95% by weight;
ethylene glycol dimethacrylate equal to or less than 5% by weight;
dye material concentrations ranging from $1 \times 10^{-6}\%$ by weight to 1% by weight.

I claim:
1. A method of forming core members from which single-piece intraocular lenses (IOL) may be machined, comprising the steps of:
    forming a thin sheet of colored polymethyl methacrylate (PMMA);
    coring the sheet to form holes therein;
    filling the holes with a clear or differently colored PMMA material;
    polymerizing the PMMA materials comprising the sheet and filled holes; and
    cutting core members from the polymerized sheet each having an inner circular region of clear or differently colored PMMA material and an outer region of colored PMMA material integral with the inner region.
2. The method of claim 1 wherein the sheet of PMMA is formed by the steps of:
    mixing methyl methacrylate, ethylene glycol dimethacrylate, a polymerization initiator, and a dye material;
    deareating the mixture;
    pouring the mixture as a sheet onto a first plate;
    covering the sheet with a second plate;
    heating the plates and sheet to polymerize the mixture; and
    separating the plates to expose the resulting PMMA sheet.
3. The method of claim 2 wherein:
    the clear or differently colored PMMA material is formed by mixing methyl methacrylate, ethylene glycol dimethacrylate and a polymerization initiator, and deareating the mixture;
    the holes in the sheet are filled by lying the sheet on a flat plate and pouring the clear or differently colored PMMA material into the holes; and
    the colored and clear or differently colored PMMA materials are polymerized by covering and heating the holefilled PMMA sheet.
4. The method of claim 3 wherein:
    the mixtures comprising the colored PMMA material and clear or differently colored PMMA material further include a polymerizable UV absorber.
5. The method of claim 4 wherein:
    the UV absorber is 2-hydroxy, 4-ethyloxyacryloxy benzophenone (UV-2098); and
    the initiator is USP-245.
6. The methods of claim 1, 2m 3 or 4 further including the step of machining a core member to form a single-piece intraocular lens (IOL) having a central lens body of clear or differently colored PMMA material and positioning loops of colored PMMA material extending from the central lens body.
7. A core member formed by the method of claim 1.
8. An intraocular lens formed by the method of claim 6 and having a central lens body and positioning loops of colored PMMA material extending from the central lens body, the central lens body being of a clear or differently colored PMMA material.

* * * * *